(12) United States Patent
Isoda et al.

(10) Patent No.: US 6,512,132 B2
(45) Date of Patent: Jan. 28, 2003

(54) AQUEOUS SOLUTION OF AMINATED SILANOL COMPOUND, USE THEREOF, AND PROCESS FOR PRODUCING THE SAME

(75) Inventors: Yuichi Isoda, Kumamoto (JP); Tomoyuki Ohba, Kumamoto (JP); Kozaburo Matsumura, Kumamoto (JP)

(73) Assignee: Chisso Corporation, Osaka (JP)

( * ) Notice: Subject to any disclaimer, the term of this patent is extended or adjusted under 35 U.S.C. 154(b) by 0 days.

(21) Appl. No.: 10/130,609

(22) PCT Filed: Sep. 19, 2001

(86) PCT No.: PCT/JP01/08154
§ 371 (c)(1),
(2), (4) Date: May 21, 2002

(87) PCT Pub. No.: WO02/26749
PCT Pub. Date: Apr. 4, 2002

(65) Prior Publication Data
US 2003/0004365 A1 Jan. 2, 2003

(30) Foreign Application Priority Data
Sep. 27, 2000 (JP) ........................................ 2000-294577

(51) Int. Cl.$^7$ .................................................. C07F 7/10
(52) U.S. Cl. ............. 556/413; 106/287.11; 106/287.12; 428/391
(58) Field of Search ..................... 556/413; 106/287.12, 106/287.11; 428/391

(56) References Cited

U.S. PATENT DOCUMENTS

| 3,810,843 A | | 5/1974 | Slusarczuk et al. |
| 5,883,276 A | * | 3/1999 | Gam et al. ............... 556/413 X |
| 6,310,170 B1 | * | 10/2001 | Johnston et al. ........ 556/413 X |

FOREIGN PATENT DOCUMENTS

| JP | 2-19385 | 1/1990 |
| JP | 4-342746 | 11/1992 |

* cited by examiner

*Primary Examiner*—Paul F. Shaver
(74) *Attorney, Agent, or Firm*—Leydig, Voit & Mayer, Ltd.

(57) ABSTRACT

The present invention relates to aqueous solutions of amino group-containing silanol compounds, glass substrates and glass fibers which are surface-treated with the solutions, and processes for the preparation of aqueous solutions of amino-containing silanol compounds.

The aqueous solutions of amino group-containing silanol compounds of the present invention are prepared by reacting 1 mole of an aminoalkylsilane with 1.5 to 10 moles of water, and distilling off a volatile organic compound by-producing during the reaction until the content becomes less than 4% by weight.

14 Claims, 2 Drawing Sheets

Peak A : Silanetriol Form
Peaks B, C, D : Oligomer Form

Peak A : Silanetriol Form
Peaks B, C, D : Oligomer Form

AQUEOUS SOLUTION OF AMINATED SILANOL COMPOUND, USE THEREOF, AND PROCESS FOR PRODUCING THE SAME

TECHNICAL FIELD

This invention relates to aqueous solutions of amino group-containing silanol compounds, glass substrates and glass fibers which are surface-treated with the solutions, and processes for the preparation of aqueous solutions of amino-containing silanol compounds.

BACKGROUND ART

Hydrolyzable silanes which have been extensively used as silane coupling agents and surface treating agents for various substrates are utilized after a hydrolyzable group in the silanes has been hydrolyzed.

Japanese Patent No. 2508554 discloses, as an example of such hydrolyzable silanes, aqueous solutions of amino group-containing silanol compounds prepared by hydrolyzing aminoalkoxysilanes and removing by-producing alcohols. The amino group-containing silanol compounds, which have undergone the hydrolysis and removal of the by-producing alcohols, are materials wherein a volatile organic compound such as an alcohol is relatively difficult to generate when used in the surface treatment.

However, the aqueous solutions of amino group-containing silanol compounds disclosed in Japanese Patent No. 2508554 might lack storage stability, depending on storage conditions. Moreover, when the aqueous solutions of amino group-containing silanol compounds were allowed to stand in contact with air, ethyl alcohol exceeding 1000 ppm (0.1 MPa, 25° C.) which is an allowable concentration advised by the American Conference of Governmental Industrial Hygienists (ACGIH) might be emitted into air, depending on the conditions under which they are allowed to stand.

DISCLOSURE OF THE INVENTION

We have made intensive studies in view of the problems in the above-mentioned prior art, and found that an aqueous solution of an amino group-containing silanol compound containing less than 4% by weight of a by-producing volatile organic compound is excellent in storage stability and can control the emission of a volatile organic compound into air below the allowable concentration, said silanol compound being prepared by reacting 1 mole of an aminoalkyl silane represented by the formula (1) with 1.5 to 10 moles of water and distilling off a volatile organic compound by-producing during the reaction. The present invention has been accomplished on the basis of this finding.

$$H_2N(CH_2)_nSi(R)_3 \quad (1)$$

wherein R is a hydrolyzable group and n is an integer of 1–6.

The present invention is composed of the following items (1) to (14).

(1) An aqueous solution of an amino group-containing silanol compound containing less than 4% by weight of a by-producing volatile organic compound, prepared by reacting 1 mole of an aminoalkylsilane represented by the formula (1) with 1.5 to 10 moles of water and distilling off a volatile organic compound by-producing during the reaction.

$$H_2N(CH_2)_nSi(R)_3 \quad (1)$$

wherein R is a hydrolyzable group and n is an integer of 1 to 6.

(2) The aqueous solution of an amino group-containing silanol compound containing less than 4% by weight of a by-producing volatile organic compound according to the item 1, wherein the content of silicon is in the range of 7.5 to 17% by weight.

(3) The aqueous solution of an amino group-containing silanol compound containing less than 4% by weight of a by-producing volatile organic compound according to the item 1, wherein it is prepared using an aminoalkylsilane of the formula (1) wherein R is an alkylalkoxy group of 1 to 4 carbon atoms.

(4) The aqueous solution of an amino group-containing silanol compound containing less than 4% by weight of a by-producing volatile organic compound according to the item 1, wherein it is prepared by carrying out the reaction of an aminoalkylsilane with water and the removal of a by-producing volatile organic compound by distillation in the range of 0 to 150° C.

(5) The aqueous solution of an amino group-containing silanol compound containing less than 4% by weight of a by-producing volatile organic compound according to the item 1, wherein it is prepared by distilling off a by-producing volatile organic compound under reduced pressure in the range of 1 Pa to 0.1 MPa.

(6) The aqueous solution of an amino group-containing silanol compound containing less than 4% by weight of a by-producing volatile organic compound according to the item 1, wherein it is prepared by adding to a reaction solution water of the same weight as the volatile organic compound distilled off from the reaction solution, in the distillation of the by-producing volatile organic compound.

(7) A surface treating agent comprising the aqueous solution of an amino group-containing silanol compound as defined in any one of the preceding items 1 to 6.

(8) A glass substrate which is surface treated with the aqueous solution of an amino group-containing silanol compound as defined in any one of the preceding items 1 to 6.

(9) A glass fiber which is surface treated with the aqueous solution of an amino group-containing silanol compound as defined in any one of the preceding items 1 to 6.

(10) A process for the preparation of an aqueous solution of an amino group-containing silanol compound, which comprises reacting 1 mole of an aminoalkylsilane of the formula (1) as set forth in the item 1 with 1.5 to 10 moles of water and distilling off a volatile organic compound by-producing during the reaction until its content is less than 4% by weight.

(11) The process for the preparation of an aqueous solution of an amino group-containing silanol compound according to the item 10, wherein the aminoalkylsilane of the formula (1) as defined in the item 1 wherein R is an alkylalkoxy group of 1 to 4 carbon atoms is used.

(12) The process for the preparation of an aqueous solution of an amino group-containing silanol compound according to the item 10, wherein the reaction of an aminoalkylsilane with water and the removal of a by-producing volatile organic compound by distillation are carried out in the range of 0 to 150° C.

(13) The process for the preparation of an aqueous solution of an amino group-containing silanol compound according to the item 10, wherein the by-producing volatile organic compound is distilled off under reduced pressure in the range of 1 Pa to 0.1 MPa.

(14) The process for the preparation of an aqueous solution of an amino group-containing silanol compound according to the item 10, wherein water of the same weight as the volatile organic compound removed by distillation from a reaction solution is added to the reaction solution, in the distillation of the by-producing volatile organic compound.

BEST MODE FOR CARRYING OUT THE INVENTION

Figure 1:
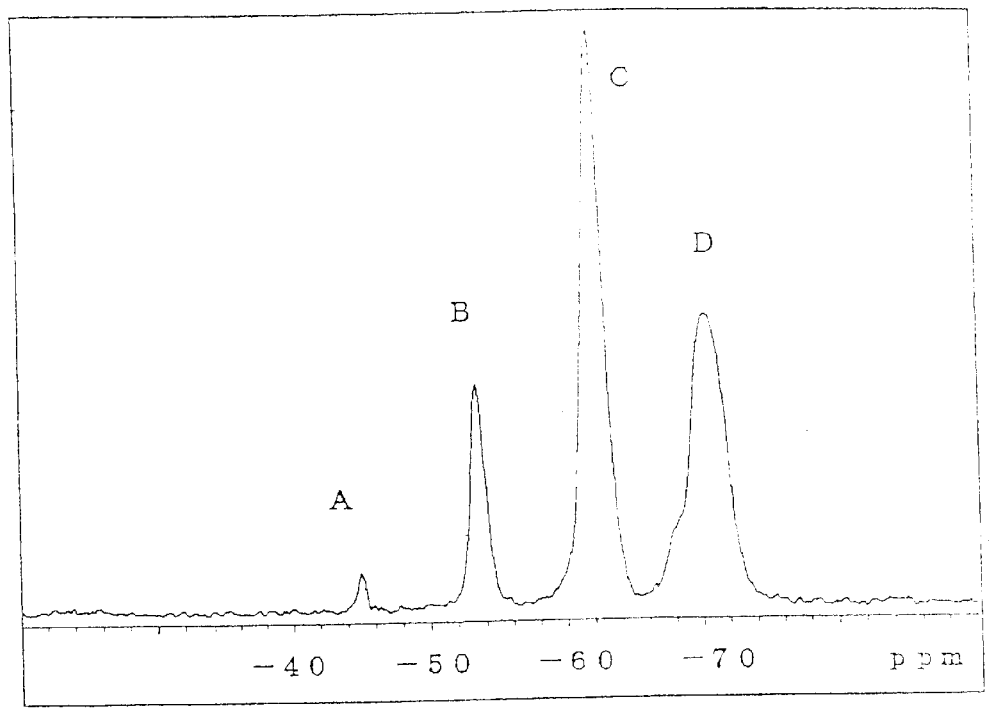
FIG. 1 is a $^{29}$Si-NMR chart before dilution of an aqueous solution of an amino group-containing silanol compound.

The invention is described in detail below.

In the formula (I) of the invention, n is an integer of 1 to 6, preferably 1 to 4, and more preferably 3. A hydrolyzable silane containing an aminopropyl group wherein n is 3 has good water-solubility. The aminoalkyl silanes represented by the formula (1) according to the invention may be commercially available ones.

In the invention, R in the formula (1) is not particularly limited, so long as it is a hydrolyzable group. Preferably, R is an alkylalkoxy group of not more than 4 carbon atoms. Examples of such a hydrolyzable group include methoxy, ethoxy, isopropoxy and the like. If R is an alkylalkoxy group of not more than 4 carbon atoms, a volatile organic compound producing by the hydrolysis has a relatively low boiling point, and is easily removed from the reaction solution.

In the reaction of the aminoalkoxysilane of the formula (1) with water (hydrolysis reaction), if the proportion of water used in the reaction is less than 1.5 moles per one mole of the aminoalkoxysilane, the reaction may not proceed sufficiently and the hydrolyzable group may remain unreacted. If the proportion exceeds 10 moles per one mole of the aminoalkoxysilane, the efficiency in the distillation of the volatile organic compound subsequent to the hydrolysis reaction may deteriorate.

In the invention, the temperature for the hydrolysis is not particularly limited, but it is preferably in the range of 0 to 150° C., more preferably 40 to 120° C.

A method for distilling off the volatile organic compound by-producing in the hydrolysis reaction is not particularly limited, but the distillation is carried out preferably under the pressure of 1 Pa to 0.1 MPa. The temperature is preferably in the range of 0 to 150° C., more preferably 40 to 120° C., but not limited thereto.

In the invention, the by-producing volatile organic compound is distilled off until its content becomes less than 4% by weight relative to the aqueous solution of an amino group-containing silanol compound. The content of the organic compound is less than 4% by weight, but it is preferably 2% by weight.

The temperature for the hydrolysis and the temperature for distilling off the by-producing volatile organic compound are as described above. The hydrolysis and the distilling off are preferably carried out in the range of 0 to 150° C. in view of good efficiency and no deterioration of the product.

In the distillation of the by-producing volatile organic compound according to the invention, it is preferable to add to a reaction solution water of the same weight as the volatile organic compound to be removed from the reaction solution by distillation. This addition can prevent condensation of the reaction solution and the resultant increase in the viscosity and reduction in the efficiency of distillation.

In the invention, the proportion of silicon contained in the aqueous solution of an amino group-containing silanol compound is preferably in the range of 7.5 to 17% by weight, based on the weight of the aqueous solution. If it is more than 17% by weight, the viscosity of the aqueous solution tends to exceedingly increase, thereby lowering the flowability, which leads to the difficulty in keeping the quality constant. If it is less than 7.5% by weight, the storage stability of the aqueous solution may decrease, resulting in the occurrence of coloration or the like.

The proportion of silicon contained in the aqueous solutions of an amino group-containing silanol compound can be controlled in such a manner that the concentration of an amino group-containing silanol compound is determined as a nonvolatile matter and adjusted to 30–67% by weight by dilution with water or by distillation operation. The proportion of silicon contained can be confirmed by a known method for measuring the content of silicon.

The aqueous solution of an amino group-containing silanol compound according to the invention is clear and colorless or slightly yellowish. Since the content of the volatile organic compound upon the production is less than 4% by weight, the emission of a volatile organic compound into air at ordinary temperature and pressure can be controlled below the allowable concentration advised by the American Conference of Governmental Industrial Hygienists (ACGIH). Since the by-producing volatile organic compound is removed after complete hydrolysis of the hydrolyzable group, the content of the by-producing volatile organic compound does not increase more than the level contained upon the production, even if said aqueous solution is diluted further with water.

After completion of the removal of the by-producing volatile organic compound by distillation, the concentration of the amino group-containing silanol compounds in the reaction solution may be measured and, if necessary, adjusted to any level within the range not impairing the effects of the invention by dilution with water or by concentration with re-distillation.

As the concentration of the aqueous solution of an amino group-containing silanol compound is lower, the content of a silanetriol form having a monomer structure more increases. However, the aqueous solution also contains an oligomer compound which is considered to improve the film-forming properties of the solution when used as a surface treating agent. In addition, the aqueous solution of an amino group-containing silanol compound are very stable, and no alteration is observed in the content of a volatile organic compound, the average composition and appearance even after the storage test was carried out.

The aqueous solutions of an amino group-containing silanol compound are useful as silane coupling agents or surface treating agents.

The composition and physical properties of the surface treating agents of the invention are not particularly limited, so long as those agents comprise the aqueous solution of an amino group-containing silanol compound of the invention. The surface treating agents may contain pigments, antifoaming agents, lubricants, preservatives, pH adjustors, film-forming agents, antistatic agents, antibacterial agents, surface active agents, dyestuffs or the like, within the range not impairing the effects of the invention.

The proportion of the aqueous solution of an amino group-containing silanol compound contained in the surface treating agent of the invention is preferably in the range of 0.1 to 50% by weight based on the treating agent.

The uses of the aqueous solutions of an amino group-containing silanol compound and the surface treating agents comprising the same can include, but not limited to, treatment of glass fibers, liquid sealing agents, casting molds, resin concrete, surface modification of resins, additives for water-based coatings or the like. When they are used in the surface treatment of glass fibers and glass substrates such as glass plates, especially desirable effects are obtained due to good wetting and good adherence to the surface of glass substrates, which are characteristics of aminosilane.

EXAMPLES

The invention is further illustrated by the following examples.

Preparation of Aqueous Solution of an Amino Group-containing Silanol Compound

Example 1

In a 2-liter flask, equipped with a distillation column having a device for measuring a temperature at the top, a device for measuring an internal temperature, a stirrer, a liquid feeding device, a cooler and a receiver for distillate, 1000 g of 3-aminopropyltriethoxysilane (Saira Ace S330 manufactured by Chisso Corporation) were charged, and then 500 g of deionized water were introduced from the liquid feeding device. The point at which the peak of 3-aminopropyltriethoxysilane disappeared, indicating the completion of hydrolysis was determined by gas chromatography. Subsequently, the pressure within the reaction vessel was reduced to 0.02 MPa, and a reaction solution in the flask was heated to 60° C. to remove 500 g of ethanol by-produced. To remove trace amounts of residual ethanol, distillation was further continued to remove 250 g of ethanol distillate. Then, deionized water of the same weight as the ethanol distillate was added to the reaction solution to adjust the concentration and viscosity, thereby affording an aqueous solution of an amino group-containing silanol compound.

The reaction solution after completion of the distillation was analyzed by gas chromatography. The ethanol content was found to be not more than 0.1% by weight. An aliquot of the aqueous solution of the amino group-containing silanol compound was measured into an aluminum cup and heated to dryness in a hot-air oven at 105° C. for 3 hrs. The nonvolatile matter was found to be 50% by weight. It was found that the content of silicon in the aqueous solution of the amino group-containing silanol compound was 12.7% by weight and the viscosity at 25° C. was 150 mm$^2$/s.

Example 2

In the same 2-liter flask as used in Example 1, 660 g of 3-aminopropyltriethoxysilane (Saira Ace S330 manufactured by Chisso Corporation) were charged, and then 670 g of deionized water were introduced from the liquid feeding device. The point at which the peak of 3-aminopropyltriethoxysilane disappeared, indicating the completion of hydrolysis was determined by gas chromatography. Subsequently, the pressure within the reaction vessel was reduced to 0.02 MPa, and a reaction solution in the flask was heated to 60° C. to remove 330 g of ethanol by-produced. To remove trace amounts of residual ethanol, distillation was further continued to remove 250 g of ethanol distillate. Then, deionized water of the same weight as the ethanol distillate was added to the reaction solution to adjust the concentration and viscosity, thereby affording an aqueous solution of an amino group-containing silanol compound.

The aqueous solution of the amino group-containing silanol compound after completion of the distillation was analyzed by gas chromatography. The ethanol content was found to be not more than 0.1% by weight. An aliquot of the aqueous solution of the amino group-containing silanol compound was measured into an aluminum cup and heated to dryness in a hot-air oven at 105° C. for 3 hrs. The nonvolatile matter was found to be 33% by weight. It was found that the content of silicon in the aqueous solution of the amino group-containing silanol compound was 8.2% by weight and the viscosity at 25° C. was 9 mm$^2$/s.

Comparative Example 1

In the same 2-liter flask as used in Example 1, 400 g of 3-aminopropyltriethoxysilane (Saira Ace S330 manufactured by Chisso Corporation) were charged, and then 800 g of deionized water were introduced from the liquid feeding device. The point at which the peak of 3-aminopropyl triethoxysilane disappeared, indicating the completion of hydrolysis was determined by gas chromatography. Subsequently, the pressure within the reaction vessel was reduced to 0.02 MPa, and a reaction solution in the flask was heated to 60° C. to remove 200 g of ethanol by-produced. To remove trace amounts of residual ethanol, distillation was further continued to remove 250 g of ethanol distillate. Then, deionized water of the same weight as the ethanol distillate was added to the reaction solution to adjust the concentration and viscosity, thereby affording an aqueous solution of an amino group-containing silanol compound.

The reaction solution after completion of the distillation was analyzed by gas chromatography. The ethanol content was found to be not more than 0.1% by weight. An aliquot of the aqueous solution of the amino group-containing silanol compound was measured into an aluminum cup and heated to dryness in a hot-air oven at 105° C. for 3 hrs. The nonvolatile matter was found to be 20% by weight. It was found that the content of silicon in the aqueous solution of the amino group-containing silanol compound was 5.1% by weight and the viscosity at 25° C. was 2 mm$^2$/s.

Storage Test

After the aqueous solutions of the amino group-containing silanol compound prepared in Examples 1, 2 and Comparative Example 1 were stored at 40° C. for 180 days, the analysis of the viscosity, composition and alcohol content was carried out.

For the solutions of Examples 1, 2 and Comparative Example 1, the viscosity was constant for 180 days. (Table 1). The viscosity was measured in accordance with JIS Z 8803.

During the storage period of 180 days, an increase in the alcohol content was not observed in the aqueous solutions of Examples 1, 2 and Comparative Example 1 (Table 2). The alcohol content was measured by gas chromatography.

For the aqueous solutions of the amino group-containing silanol compound prepared in Examples 1 and 2, no coloration was detectable by visual observation. For the aqueous solution of the amino group-containing silanol compound prepared in Comparative Example 1, however, the analysis value for coloration (haze) varied 20 or more, and yellowing was apparently observed by visual observation (Table 3). The coloration analysis was determined in accordance with JIS K0071.

From the results of these storage tests, it was found that the aqueous solutions of the amino group-containing silanol compound prepared by the invention were very stable.

TABLE 1

| | Viscosity ($10^{-6}$ m$^2$/s 25° C.) | | |
|---|---|---|---|
| Lapsed days (day) | Example 1 | Example 2 | Comparative Example 1 |
| 0 | 150 | 9 | 2 |
| 90 | 151 | 9 | 3 |
| 180 | 149 | 9 | 2 |

TABLE 2

| | Alcohol content (% by weight) | | |
|---|---|---|---|
| Lapsed days (day) | Example 1 | Example 2 | Comparative Example 1 |
| 0 | <0.1 | <0.1 | <0.1 |
| 90 | <0.1 | <0.1 | <0.1 |
| 180 | <0.1 | <0.1 | <0.1 |

TABLE 3

| | Before storage test | | After storage of 180 days | |
|---|---|---|---|---|
| Sample | Appearance (Visual observation) | Color (Haze) | Appearance (Visual observation) | Color (Haze) |
| Example 1 | Colorless, clear | 30 | Colorless, clear | 30 |
| Example 2 | Colorless, clear | 30 | Colorless, clear | 30 |
| Comparative Example 1 | Colorless, clear | 30 | Yellow, clear | 50 |

Analysis of Alcohol Content

The aqueous solution of the amino group-containing silanol compound prepared in Example 1 (50% by weight of nonvolatile matter) was diluted with deionized water such that the nonvolatile matter was 33%, 20%, 10% and 1% by weight. By analysis of the alcohol content by gas chromatography, no formation of alcohol was observed.

Analysis of Composition of Effective Compound

Figure 2:
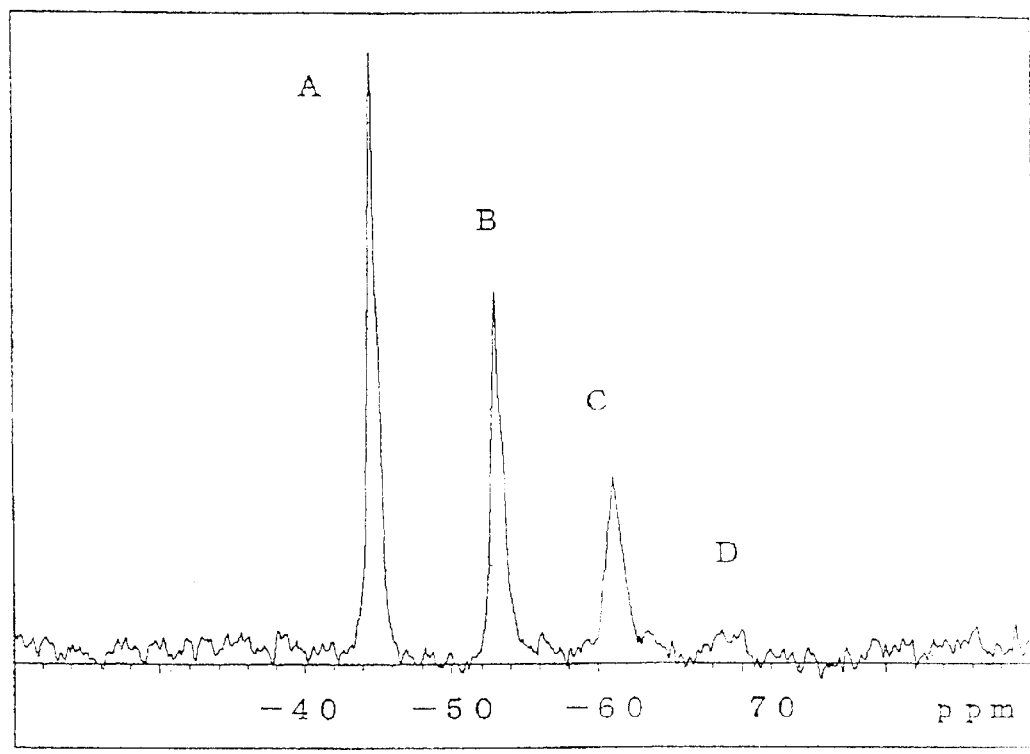
FIG. 2 is a $^{29}$Si-NMR chart after dilution of an aqueous solution of an amino group-containing silanol compound.

An average composition of each diluted solution prepared in the above "Analysis of alcohol content" was analyzed by $^{29}$Si-NMR. When the aqueous solution of the amino group-containing silanol compound prepared in Example 1 was diluted to make the concentration of the compound lower, the silane triol form increased as compared with the original aqueous solution of the amino group-containing silanol compound (Example 1). Especially when the aqueous solution was diluted to 1% by weight of the nonvolatile matter, 45 mole % of the composition was composed of the silane triol form (FIG. 1, FIG. 2). However, 55 mole % of an oligomer compound was present, which exhibited good film-forming properties when the aqueous solution was used as a surface treating agent.

Accordingly, it was found that the aqueous solutions of amino group-containing silanol compounds of the present invention did not produce alcohol even diluted with water, and that they contained sufficiently the oligomer compound as the effective compound for the surface treatment (Table 4).

TABLE 4

| Concentration of nonvolatile matter (% by weight) | Content of oligomer form (mol %) |
|---|---|
| 50 | 99 |
| 33 | 98 |
| 20 | 96 |
| 10 | 90 |
| 1 | 55 |

Evaluation as a Surface Treating Agent

Surface treating agent (1) having 5% by weight of nonvolatile matter was prepared by adding 90 g of deionized water to 5 g of the aqueous solution of the amino group-containing silanol compound prepared in Example 1. For comparison, Surface treating agent (2) having 5% by weight of nonvolatile matter was prepared by adding 95 g of deionized water to 5 g of 3-aminopropyltriethoxysilane (Saira Ace S330 manufactured by Chisso Corporation).

Each of the surface treating agents was stirred for one hour, and then coated onto a slide glass and the wetting property was evaluated by visual observation. The slide glass was washed successively with a detergent, deionized water, acetone and deionized water, and air-dried. The coating of the surface treating agent was carried out by dipping. As a result, it was found that there was no difference in the wetting property in each concentration, and the performance was hold even if the volatile organic compound (VOC) was reduced (Table 5).

TABLE 5

| Sample | Evaluation |
|---|---|
| Surface treating agent (1): prepared from Example 1 | ○ |
| Surface treating agent (2): prepared from 3-aminopropyltriethoxysilane | ○ |

INDUSTRIAL APPLICABILITY

The aqueous solutions of amino group-containing silanol compounds of the present invention are excellent in storage stability and can control the emission of a volatile organic compound into air below the allowable concentration. Further, the surface treating agents of the present invention contain very low volatile organic compounds, and hence are suitable as easily disposable surface treating agents when used in the treatment of glass fibers in which aminosilanes have been used, liquid sealing agents, casting molds, resin concrete, surface modification of resins, additives for water-based coatings or the like.

What is claimed is:

1. An aqueous solution of an amino group-containing silanol compound containing less than 4% by weight of a by-producing volatile organic compound, prepared by reacting 1 mole of an aminoalkylsilane represented by the formula (1) with 1.5 to 10 moles of water and distilling off a volatile organic compound by-producing during the reaction:

$$H_2N(CH_2)_nSi(R)_3 \tag{1}$$

wherein R is a hydrolyzable group and n is an integer of 1 to 6.

2. The aqueous solution of an amino group-containing silanol compound containing less than 4% by weight of a by-producing volatile organic compound according to claim 1, wherein the content of silicon is in the range of 7.5 to 17% by weight.

3. The aqueous solution of an amino group-containing silanol compound containing less than 4% by weight of a by-producing volatile organic compound according to claim 1, wherein it is prepared with an aminoalkylsilane of the formula (1) wherein R is an alkylalkoxy group of 1 to 4 carbon atoms.

4. The aqueous solution of an amino group-containing silanol compound containing less than 4% by weight of a by-producing volatile organic compound according to claim 1, wherein it is prepared by carrying out the reaction of an aminoalkylsilane with water and the removal of a by-producing volatile organic compound by distillation, in the range of 0 to 150° C.

5. The aqueous solution of an amino group-containing silanol compound containing less than 4% by weight of a by-producing volatile organic compound according to claim 1, wherein it is prepared by distilling off a by-producing volatile organic compound under reduced pressure in the range of 1 Pa to 0.1 MPa.

6. The aqueous solution of amino group-containing silanol compounds containing less than 4% by weight of a by-producing volatile organic compound according to claim 1, wherein it is prepared by adding to a reaction solution water of the same weight as the volatile organic compound to be removed by distillation from the reaction solution, in the distillation of the by-producing volatile organic compound.

7. A surface treating agent comprising the aqueous of an amino group-containing silanol compound as defined in claim 1.

8. A glass substrate which is surface treated with the aqueous solution of an amino group-containing silanol compound as defined in claim 1.

9. A glass fiber which is surface treated with the aqueous solution of an amino group-containing silanol compound as defined in claim 1.

10. A process for the preparation of an aqueous solution of an amino group-containing silanol compound, which comprises reacting 1 mole of an aminoalkylsilane represented by the formula (1) as set forth in claim 1 with 1.5 to 10 moles of water and distilling off a volatile organic compound by-producing during the reaction until its content becomes less than 4% by weight.

11. The process for the preparation of an aqueous solution of an amino group-containing silanol compound according to claim 10, wherein the aminoalkylsilane of the formula (1) as defined in claim 1 wherein R is an alkylalkoxy group of 1 to 4 carbon atoms is used.

12. The process for the preparation of an aqueous solution of an amino group-containing silanol compound according to claim 10, wherein the reaction of an aminoalkylsilane with water and the removal of a by-producing volatile organic compound by distillation are carried out in the range of 0 to 150° C.

13. The process for the preparation of an aqueous solution of an amino group-containing silanol compound according to claim 10, wherein the by-producing volatile organic compound is distilled off under reduced pressure in the range of 1 Pa to 0.1 MPa.

14. The process for the preparation of an aqueous solution of an amino group-containing silanol compound according to claim 10, wherein water of the same weight as the volatile organic compound removed by distillation from a reaction solution is added to the reaction solution, in the distillation of the by-producing volatile organic compound.

* * * * *

UNITED STATES PATENT AND TRADEMARK OFFICE
CERTIFICATE OF CORRECTION

PATENT NO.    : 6,512,132 B1
DATED         : January 28, 2003
INVENTOR(S)   : Isoda et al.

It is certified that error appears in the above-identified patent and that said Letters Patent is hereby corrected as shown below:

<u>Column 5,</u>
Lines 28 and 57, change "Saira Ace" to -- Sila-Ace --.

<u>Column 6,</u>
Line 20, change "Saira Ace" to -- Sila-Ace --.

<u>Column 9,</u>
Line 28, change "the aqueous of an" to -- the aqueous solution of an --.

Signed and Sealed this

Twenty-second Day of July, 2003

JAMES E. ROGAN
*Director of the United States Patent and Trademark Office*